(12) United States Patent
Zischke

(10) Patent No.: US 12,386,169 B2
(45) Date of Patent: Aug. 12, 2025

(54) WIDE FIELD OF VIEW OBJECTIVE LENS

(71) Applicant: HOYA CORPORATION, Tokyo (JP)

(72) Inventor: Holger Zischke, Munich (DE)

(73) Assignee: HOYA CORPORATION, Tokyo (JP)

( * ) Notice: Subject to any disclaimer, the term of this patent is extended or adjusted under 35 U.S.C. 154(b) by 567 days.

(21) Appl. No.: 17/619,490

(22) PCT Filed: Jul. 7, 2020

(86) PCT No.: PCT/IB2020/056363
§ 371 (c)(1),
(2) Date: Dec. 15, 2021

(87) PCT Pub. No.: WO2021/014248
PCT Pub. Date: Jan. 28, 2021

(65) Prior Publication Data
US 2022/0179188 A1    Jun. 9, 2022

(30) Foreign Application Priority Data

Jul. 19, 2019  (EP) .................................. 19187218

(51) Int. Cl.
*G02B 23/24* (2006.01)
*G02B 9/64* (2006.01)
(Continued)

(52) U.S. Cl.
CPC ....... *G02B 23/243* (2013.01); *G02B 13/0045* (2013.01); *G02B 13/06* (2013.01); *G02B 9/64* (2013.01)

(58) Field of Classification Search
CPC .. G02B 23/243; G02B 13/0045; G02B 13/06; G02B 9/64; G02B 9/62; A61B 1/00096
See application file for complete search history.

(56) References Cited

U.S. PATENT DOCUMENTS

2007/0213590 A1 *  9/2007  Squicciarini ....... A61B 1/00101
                                                          600/172
2010/0142062 A1   6/2010  Asami et al.
(Continued)

FOREIGN PATENT DOCUMENTS

CN        107436475       12/2017
CN        107924044        4/2018
(Continued)

OTHER PUBLICATIONS

Adolf W. Lohmann, "Scaling laws for lens systems," Appl. Opt. 28, 4996-4998 (Year: 1989).*
(Continued)

*Primary Examiner* — Ricky L Mack
*Assistant Examiner* — K Muhammad
(74) *Attorney, Agent, or Firm* — Greenblum & Bernstein, P.L.C.

(57) ABSTRACT

It is provided an objective lens, consisting of, in order from an object side to an image side: a first meniscus lens and a second meniscus lens, both having a convex side towards the object side; a first condensing unit; an aperture stop; a second condensing unit. An apex of the second meniscus lens is spaced apart from the first meniscus lens. A total number of lenses in the first and second condensing units is not less than 4 and not more than 6. If a radius of the first meniscus lens on the image side is denoted r2, a radius of the second meniscus lens on the object side is denoted r3, and a radius of the second meniscus lens on the image side is denoted r4, at least two of the following three conditions are fulfilled:

$r2/r4 \geq 1.40$;

$r4/r3 \geq 0.111$; and $r2/r3 \geq 0.16$.

2 Claims, 11 Drawing Sheets

(51) Int. Cl.
 *G02B 13/00* (2006.01)
 *G02B 13/06* (2006.01)

(56) References Cited

U.S. PATENT DOCUMENTS

| | | | |
|---|---|---|---|
| 2011/0037828 A1 | 2/2011 | Wakamiya | |
| 2012/0056978 A1 | 3/2012 | Abe et al. | |
| 2012/0113533 A1 | 5/2012 | Kubota et al. | |
| 2016/0299317 A1 | 10/2016 | Ikegaya | |
| 2017/0146778 A1 | 5/2017 | Jeong et al. | |
| 2017/0242220 A1* | 8/2017 | Lee | G02B 13/0045 |
| 2018/0024331 A1 | 1/2018 | Matsunaga | |
| 2018/0131874 A1 | 5/2018 | Tamura et al. | |
| 2018/0203211 A1* | 7/2018 | Kim | G02B 9/64 |
| 2018/0356616 A1 | 12/2018 | Bone et al. | |
| 2019/0079267 A1 | 3/2019 | Jung et al. | |
| 2019/0187442 A1 | 6/2019 | Jia et al. | |
| 2019/0187443 A1 | 6/2019 | Jia et al. | |
| 2019/0289209 A1* | 9/2019 | Niazi | G02B 9/34 |
| 2020/0192069 A1* | 6/2020 | Makeev | G02B 9/64 |

FOREIGN PATENT DOCUMENTS

| | | | | |
|---|---|---|---|---|
| CN | 107924044 A | * | 4/2018 | G02B 13/0045 |
| EP | 1629764 | | 3/2006 | |
| EP | 3415968 | | 12/2018 | |
| JP | 4-68307 | | 3/1992 | |
| JP | 10-309259 | | 11/1998 | |
| JP | 11-23961 | | 1/1999 | |
| JP | 2006-337691 | | 12/2006 | |
| JP | 2008-58387 | | 3/2008 | |
| JP | 2009-42377 | | 2/2009 | |
| JP | 2010-160479 | | 7/2010 | |
| JP | 2010-169885 | | 8/2010 | |
| JP | 2010-217505 | | 9/2010 | |
| JP | 2010-256627 | | 11/2010 | |
| JP | 2011-107425 | | 6/2011 | |
| JP | 2012-103319 | | 5/2012 | |
| JP | 2016-200743 | | 12/2016 | |
| JP | 2018-522266 | | 8/2018 | |
| TW | M357610 | | 5/2009 | |
| WO | 2009/150653 | | 12/2009 | |
| WO | WO-2014129156 A1 | * | 8/2014 | G02B 13/002 |
| WO | 2016/167063 | | 10/2016 | |
| WO | 2017/027749 | | 2/2017 | |

OTHER PUBLICATIONS

International Search Report issued in International Patent Application No. PCT/IB2020/056363, dated Aug. 11, 2020.
Written Opinion of the International Searching Authority issued in International Patent Application No. PCT/IB2020/056363, dated Aug. 11, 2020.
Extended European Search Report in corresponding EP Appl. No. 19187218.3, dated Jan. 21, 2020.
Office Action issued in Corresponding CN Patent Application No. 202080046285.6, dated Apr. 12, 2023, along with an English translation thereof.
Office Action issued in Corresponding EP Patent Application No. 20160417.0, dated May 2, 2023.
Office Action issued in Corresponding CN Patent Application No. 202080046285.6, dated Dec. 1, 2023, along with an English translation thereof.
Office Action issued in Corresponding JP Patent Application No. 2022-503876, dated Mar. 12, 2024, along with an English translation thereof.

* cited by examiner

WIDE FIELD OF VIEW OBJECTIVE LENS

FIELD OF THE INVENTION

The present invention relates to an objective lens with a wide field of view. In particular, it relates to an objective lens with a wide field of view which may be used in an endoscope.

BACKGROUND OF THE INVENTION

Endoscopes with an objective lens having a field of view (FOV) of more than 180° are known in the art. However, such endoscopes typically have a field of view of only slightly more than 180°. It is desired to have an endoscope with an even larger field of view.

SUMMARY OF THE INVENTION

It is an object of the present invention to improve the prior art. Namely, according to aspects of the present invention, there are provided objective lenses according to the respective independent claims. Furthermore, aspects of the invention provide a sensor system comprising the objective lens according to the former aspects and an endoscope comprising the sensor system. Further details are set out in the respective dependent claims.

According to some embodiments of the invention, at least one of the following advantages may be achieved:
- the objective lens has a wide field of view of more than 225°.
- a maximum chief ray angle in an image circle is less than 30°, such that conventional semiconductor image sensors (such as CMOS or CCD) can be employed.
- the image has small distortions, in particular small f/θ-distortion.
- even in a small-scale version which is suitable for an endoscope, the lenses can be produced without difficulty.

Further advantages become apparent from the following detailed description. It is to be understood that any of the above modifications and the examples described below can be applied singly or in combination to the respective aspects to which they refer, unless they are explicitly stated as excluding alternatives.

BRIEF DESCRIPTION OF THE DRAWINGS

Further details, features, objects, and advantages are apparent from the following detailed description of preferred embodiments of the invention, which is to be taken in conjunction with the appended drawings, wherein.

Hereinbelow, certain embodiments of the present invention are described in detail with reference to the accompanying drawings, wherein the features of the embodiments can be freely combined with each other unless otherwise described. However, it is to be expressly understood that the description of certain embodiments is given by way of example only, and that it is by no way intended to be understood as limiting the invention to the disclosed details.

Figure 1:
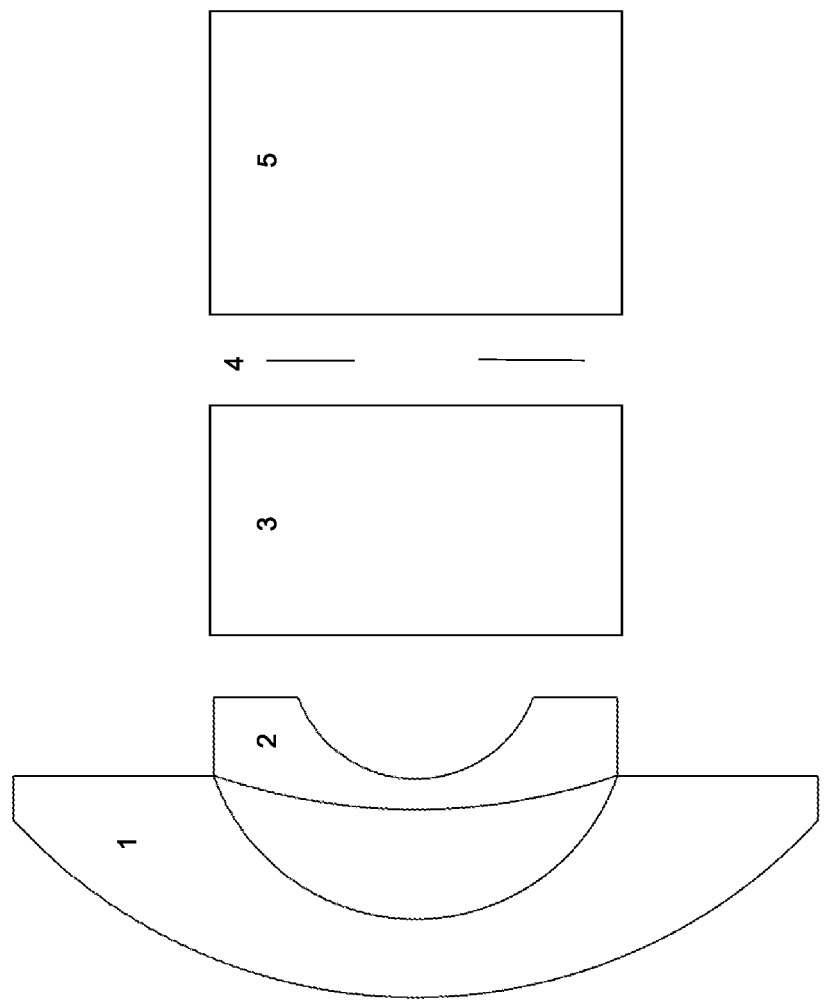
FIG. 1 depicts the general setup of the objective lens according to some embodiments of the invention.
Figure 2:
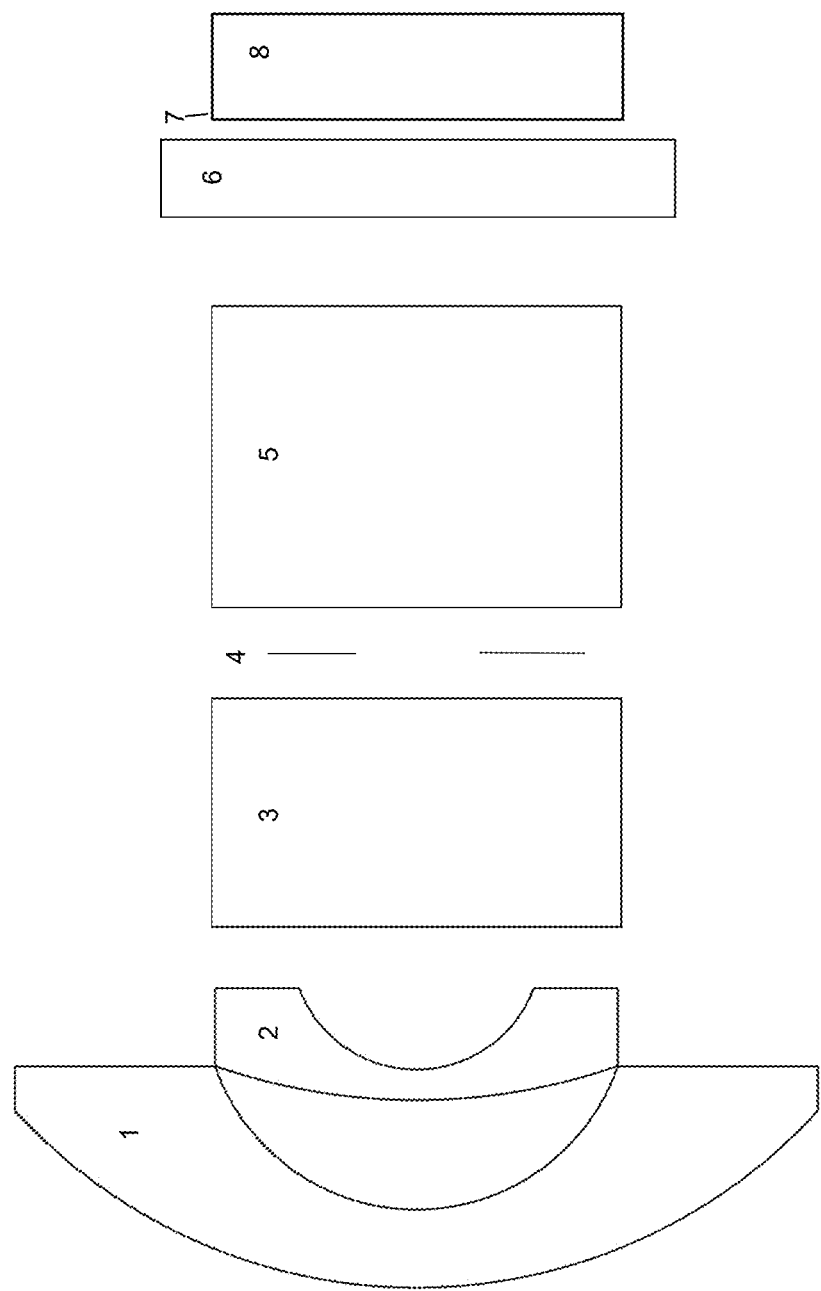
FIG. 2 shows the general setup of the sensor system according to some embodiments of the invention.

FIG. 1 shows the general setup of an objective lens according to some embodiments of the invention. Namely, the objective lens consists of, in order from an object side to an image side:

two meniscus lenses (a first meniscus lens 1 and a second meniscus lens 2), each having a convex side towards the object side; a first condensing unit 3 which condenses the light from the second meniscus lens 2; an aperture stop 4; a second condensing unit 5 which condenses the light from the aperture stop 4. Each of the first and second condensing units 3, 5 may comprise one or more lenses and the total number of lenses in the two condensing units 3, 5 is not less than four and not more than six. An apex of the second meniscus lens 2 is spaced apart from the lens surface on the image side of the first meniscus lens 1.

According to some embodiments of the invention, the radius of the first meniscus lens 1 on the image side (r2), the radius of the second meniscus lens 2 on the object side (r3) and the radius of the second meniscus lens 2 on the image side (r4) fulfil at least two of the following three conditions:

$$r2/r4 \geq 1.40 \quad (1);$$

$$r4/r3 \geq 0.111 \quad (2); \text{ and}$$

$$r2/r3 \geq 0.16 \quad (3).$$

The meaning of these conditions is as follows:

According to condition (1), the curvatures on the image side of the first and second meniscus lenses 1, 2 are substantially equal, or the curvature on the image side of the second meniscus lens 2 is stronger than that of the first meniscus lens 1. In the prior art, this quotient is typically smaller than 1, which means that the curvature of the image side of the first meniscus lens is stronger than that of the second meniscus lens. If condition (1) is not fulfilled, f/θ-distortion is enhanced. In addition, the MTF@150 lp/mm at a viewing angle of 115° decreases if condition (1) is not fulfilled (e.g. due to a decrease of r2 while r3 and r4 are maintained).

The second condition (2) defines that the curvature on the object side of the second meniscus lens 2 is much less than that on the image side of the second meniscus lens 2. However, it also defines that the curvature on the object side of the second meniscus lens 2 is not negligible compared to that on the image side.

In the prior art, the second lens of such an objective lens with a wide field of view (a fisheye objective) is substantially plano-convex, and in some cases, it may even be a biconcave lens. In contrast to the prior art, according to some embodiments of the invention, the second meniscus lens 2 is a "true" meniscus lens rather than substantially a plano-concave lens or a biconcave lens.

If condition (2) is not fulfilled, the MTF@150 lp/mm at a viewing angle of 115° decreases (e.g. due to an increase of r3 while r2 and r4 are maintained). Also, the FoV may decrease.

The third condition (3) defines that the curvature on the image side of the first meniscus lens 1 is stronger than that on the object side of the second meniscus 2 lens. That is the reason why the apex of the second meniscus lens 2 is spaced apart from the first meniscus lens 1. Condition (3) also defines that the curvature on the object side of the second meniscus lens 2 is not negligible compared to the curvature on the image side of the first meniscus lens 1. As discussed with condition (2), in the prior art, the surface on the object side of the second lens is typically substantially flat (a plano-concave lens or even a biconcave lens). In some embodiments of the invention, the curvature on the object side of the second meniscus lens 2 must not be considered as substantially flat. Thus, the surface on the image side of the first meniscus lens 1 and the surface on the object side of the second meniscus lens 2 form a kind of a meniscus air lens.

If condition (3) is not fulfilled, the MTF@150 lp/mm at a viewing angle of 115° decreases (e.g. due to a decrease of r2 while r3 and r4 are maintained, or due to a increase of r3 while r2 and r4 are maintained). Also, the FoV may decrease.

Preferably, at least one of the following conditions (1'), (2'), and (3') is fulfilled:

$$r2/r4 \geq 1.55 \tag{1'}$$

$$r4/r3 \geq 0.131 \tag{2'; and}$$

$$r2/r3 \geq 0.20 \tag{3'}$$

More preferably, at least one of the following conditions (1"), (2"), and (3") is fulfilled:

$$r2/r4 \geq 1.64 \tag{1"}$$

$$r4/r3 \geq 0.152 \tag{2"; and}$$

$$r2/r3 \geq 0.24 \tag{3"}$$

Still more preferably, at least one of the following conditions (1'''), (2'''), and (3''') is fulfilled:

$$r2/r4 \geq 1.64 \tag{1'''}$$

$$r4/r3 \geq 0.19 \tag{2'''; and}$$

$$r2/r3 \geq 0.35 \tag{3'''}$$

Preferably, at least one of the following conditions is additionally fulfilled:

$$1.98 \geq r2/r4 \tag{4}$$

$$0.35 \geq r4/r3 \tag{5; and}$$

$$0.65 \geq r2/r3 \tag{6}$$

If at least one of conditions (4) to (6) is fulfilled, it is ensured that the respective lens may be easily manufactured. That is, in these cases, it is not required that the respective surface is a half-sphere. Furthermore, the MTF@150 lp/mm at a viewing angle of 115° decreases if conditions (5) and (6) are not fulfilled (e.g. due to a larger r3 at constant r4 and r2). Also, if conditions (4) and (6) are not fulfilled (e.g. due to a larger r2 at constant r4 and r3), the MTF@150 lp/mm at a viewing angle of 115° decreases and the FoV decreases due to vignetting.

More preferably, at least one of the following conditions is additionally fulfilled:

$$1.94 \geq r2/r4 \tag{4'}$$

$$0.32 \geq r4/r3 \tag{5'; and}$$

$$0.61 \geq r2/r3 \tag{6'}$$

Still more preferably, at least one of the following conditions is additionally fulfilled:

$$r2/r4 \geq 1.90 \tag{1''''}$$

$$0.24 \geq r4/r3 \tag{5''; and}$$

$$0.40 \geq r2/r3 \tag{6''}$$

According to some embodiments of the invention, the objective lens has a field of view of not less than 225°. Preferably, the field of view is not less than 230°, or even not less than 234°. On the other hand, in order to facilitate manufacturing of the objective lens, the field of view may be not more than 240°, preferably not more than 236°.

Note that the field of view is defined such that the image circle of a sphere having a distance of 8 mm from the apex of the first meniscus lens has a diameter of 2.08 mm to 2.18 mm, and a chief ray angle is not larger than 28° at each position in the image circle. Thus, a conventional semiconductor image detector, such as Omnivision OV5670, may be used to capture the image without vignetting.

According to some embodiments of the invention, if a radius of the first meniscus lens 1 on the object side is denoted r1, the following condition (7) is fulfilled:

$$4.0 \leq r1/r4 \leq 7.6 \tag{7}$$

More preferably, one of the following conditions (7') and (7") is fulfilled:

$$4.0 \leq r1/r4 \leq 6.0 \tag{7'}$$

$$4.5 \leq r1/r4 \leq 5.5 \tag{7"}$$

A diameter of the first meniscus lens 1 may not be larger than 7 mm in order to easily include the objective lens into an endoscope. However, generally, the diameter of the first meniscus lens 1 is not limited, e.g. if the objective lens is applied differently than in an endoscope.

According to some embodiments of the invention, the sum of the refractive indices of the first and second meniscus lenses 1, 2 is not less than 3.56, and/or a sum of the Abbe-numbers of the first and second meniscus lenses is not less than 58. The refractive indices are determined at a wavelength of 587.6 nm. The Abbe number is defined as $vd=(n_d-1)/(n_F-n_C)$, wherein $n_d$, $n_F$ and $n_C$ are the refractive indices of the material at the wavelengths of the Fraunhofer d-, F- and C-spectral lines (587.6 nm, 486.1 nm, and 656.3 nm, respectively). Preferably, the sum of the refractive indices is not less than 3.8 or even not less than 4. Correspondingly, the sum of the Abbe-numbers is preferably not less than 60 and even more preferable not less than 70.

According to some embodiments, the first condensing unit 3 consists of one, two, or three lenses. For example, the first condensing unit 3 may consist of a single biconvex lens. As another example, the first condensing unit 3 may consist of a biconvex lens and a meniscus lens having a concave side towards the object side. These lenses may be cemented. As a still further option, the first condensing unit 3 may consist of a meniscus lens having a concave side towards the object side and a plano-convex lens. As an example with three lenses, the first condensing unit 3 may consist of a biconcave lens, and two plano-convex lenses, wherein the biconcave lens and the first of two plano-convex lenses may be cemented. As another option, the first condensing unit 3 may consist of a plano-concave lens and a plano-convex lens, wherein the two planar surfaces may be cemented, and a plano-convex lens. These examples are not limiting.

Correspondingly, the second condensing unit 5 may consist of two, three or four lenses. For example, the second condensing unit 5 may consist of a single unit (cemented lenses) comprising two or three lenses, which may be cemented. This unit may also be useful to correct chromatic aberration and to ensure that the chief ray angle is not larger than a predetermined value such as 30° or preferably 28°.

In addition, the second condensing unit 5 may comprise a further unit consisting of a single lens or a doublet, wherein the further unit is closer to the aperture stop than the former unit. These examples are not limiting.

According to some embodiments of the invention, the objective lens has small distortions. For example, the modulation transfer function (MTF) at 300 line pairs per mm (MTF@300 lp/mm) is larger than 13% (preferably larger than 15%) at a viewing angle of 0°, MTF@150 lp/mm is larger than 22% (preferably larger than 25%) at a viewing angle of 115°, and MTF@100 lp/mm is larger than 45% (preferably larger than 50%) at all viewing angles.

A sensor system according to some embodiments of the invention comprises the objective lens as described above and a sensor device 8 for converting an image which is formed by the objective lens on a sensor area (light sensitive area) 7 into an electrical signal. For example, the sensor device 8 may be a CCD device or a CMOS device comprising a lot of pixels arranged in an array. A pixel pitch may be 0.9 µm to 1.4 µm, and in particular 1.12 µm.

Typically, the sensor device 8 is covered by a cover glass 6 which covers the sensor area 7. In this case, the cover glass 6 is located between the second condensing unit 5 and the sensor area 7.

A length through the lens from an apex of the first meniscus lens 1 to the sensor area 7 may not be more than 10 mm. Thus, the sensor system is particular suitable for an endoscope. The sensor system may be optimized to image a sphere located 8 mm in front of the apex of the first meniscus lens 1. In this case, the image circle should fit to the sensor area 7 of the sensor device 8. That is, the image circle is included in the sensor area 7. In an example, the image circle may have a diameter of not less than 2.08 mm and not more than 2.20 mm.

However, in some embodiments, the image circle includes the sensor area 7, or a major part of the sensor area 7 and the image circle overlap (e.g. more than 70%, more preferably more than 80%, or more preferably more than 90%). In some embodiments, if the diameter of the image circle is denoted di, the field of view of the objective lens is denoted FOV, a diameter of the first meniscus lens 1 is denoted d1, and an F-number of the objective lens is denoted F, the following condition (8) may be fulfilled:

$$55 \leq (di*FOV)/(d1*F) \quad (8).$$

In addition, the following condition (9) may be fulfilled:

$$(di*FOV)/(d1*F) \leq 140 \quad (9).$$

In some embodiments, the lower limit according to condition (8) may be preferably 60 or 64. In some embodiments, the upper limit according to condition (9) may be preferably 135 or 131.

According to condition (8), the space is used particularly effective.

As already mentioned several times, the objective lens and the sensor device 8 may be used in an endoscope 9 comprising a tube 10 and a head 11. The head 11 is arranged at a distal end 12 of the tube 10. The head 11 may comprise the sensor system as defined hereinabove.

In the context of the present application, the term lens defines a transparent body having a front surface and a rear surface and a medium with an effective index larger than 1. The refractive index is (substantially) homogeneous throughout the lens. Typically, the lens surfaces are spherical. However, the lens surface may be aspherical, as long as it deviates from a spherical surface by not more than 10% (preferably 5%, more preferably 2%) of the respective radius. Typically, a material of the lenses is a glass. However, in some embodiments, one or more of the lenses may be made of plastic.

The front lens (first meniscus lens) should preferably have a high resistance against acids and/or bases. The front lens should preferably be highly scratch resistant.

One or more of the lenses may have an antireflective coating or a coating to enhance resistance against acids and/or bases and/or to enhance scratch resistance. As long as this coating is not thicker than 10% (preferably 5%, more preferably 1%) of the maximum thickness of the lens, these coatings are included in the definition of the lens, although these coatings typically have a different refractive index than the remainder of the lens.

In FIGS. 3 to 10 and corresponding Tables 1 to 8, embodiments 1 to 8 of the invention are specified at greater detail. Each of these figures shows a cross-sectional view through a sensor system comprising an objective lens according to some embodiments of the invention. In addition, a central light path and a light path at an extremal FOV are shown. The Tables indicate the respective lens parameters. Radiuses, thicknesses, and clear diameters are indicated in mm. Table 9 summarizes some of the relevant parameters of the invention for embodiments 1 to 8. Table 10 indicates the refractive indices and Abbe numbers of the glasses used for embodiments 1 to 8 of the invention. However, the invention is not limited to these glasses.

TABLE 1

Lens data of Embodiment 1

| Surf | Radius | Thickness | Glass | Clear |
|---|---|---|---|---|
| OBJ | 10 | 8 | | Diam 0 |
| 1 | 4.55868 | 0.45 | N-LASF31A | 6.997118 |
| 2 | 2.025763 | 0.83 | | 3.897222 |
| 3 | 3.325 | 0.2 | N-LASF31A | 3.924294 |
| 4 | 1.05 | 1.019041 | | 2.095081 |
| 5 | −14.08837 | 0.199991 | N-ZK7 | 2.092911 |
| 6 | 2.237832 | 2.050761 | S-LAH88 | 1.824766 |
| 7 | −12.34576 | 0.01991829 | | 2 |
| STO | Infinity | 0.0197823 | | 0.508221 |
| 9 | 2.659707 | 1.1507 | N-LAK34 | 2 |
| 10 | −1.874717 | 0.01963665 | | 2 |
| 11 | 2.117432 | 0.7167899 | S-LAH97 | 1.588087 |
| 12 | −1.054733 | 0.4242363 | S-NPH3 | 1.591373 |
| 13 | −5.81968 | 0.1999944 | S-NPH2 | 1.756799 |

TABLE 1-continued

Lens data of Embodiment 1

| Surf | Radius | Thickness | Glass | Clear |
|---|---|---|---|---|
| 14 | 8.599747 | 0.196 | | 1.828844 |
| 15 | Infinity | 0.4 | N-ZK7 | 2.4 |
| 16 | Infinity | 0.04 | | 2.4 |
| IMA | Infinity | | | 2.127379 |

TABLE 2

Lens data of Embodiment 2

| Surf | Radius | Thickness | Glass | Clear Diam |
|---|---|---|---|---|
| OBJ | 10 | 8 | | 0 |
| 1 | 4.1 | 0.45 | N-LASF31A | 5.8 |
| 2 | 1.78 | 0.65 | | 3.3 |
| 3 | 3.164661 | 0.2 | N-LASF31A | 3.3 |
| 4 | 0.985 | 0.78 | | 1.854 |
| 5 | −3.73 | 0.23 | N-BAK4 | 1.854 |
| 6 | 3.690252 | 0.67 | S-LAH79 | 2.2 |
| 7 | −20.7 | 0.02008416 | | 2.2 |
| 8 | 1.685 | 0.79 | S-LAH59 | 1.8 |
| 9 | Infinity | 0.01991532 | | 1.2488 |
| STO | Infinity | 0.1198657 | | 0.4533332 |
| 11 | −7.76 | 0.6196602 | S-LAL19 | 1.2488 |
| 12 | −1.26 | 0.01985869 | | 1.8 |
| 13 | 2.175186 | 0.7 | S-LAH59 | 1.48 |
| 14 | −0.91 | 0.48 | S-NPH3 | 1.48 |
| 15 | 13.1 | 0.165 | | 1.8 |
| 16 | Infinity | 0.4 | N-ZK7 | 2.8 |
| 17 | Infinity | 0.04 | | 2.8 |
| IMA | Infinity | | | 2.088328 |

TABLE 3

Lens data of Embodiment 3

| Surf | Radius | Thickness | Glass | Clear Diam |
|---|---|---|---|---|
| OBJ | 10 | 8 | | 0 |
| 1 | 4 | 0.79 | N-LASF31A | 6.37094 |
| 2 | 1.55 | 0.8 | | 2.945 |
| 3 | 4 | 0.2 | S-LAH88 | 2.945 |
| 4 | 0.8 | 0.48 | | 1.52 |
| 5 | 4 | 1.78 | S-LAH55 | 2 |
| 6 | −2 | 0.02 | | 2 |
| STO | Infinity | 0.01975939 | | 0.3647792 |
| 8 | 10.75 | 0.99 | S-LAL7 | 2 |
| 9 | −1.2 | 0.125 | | 2 |
| 10 | 3.5 | 0.6450499 | S-LAH59 | 1.4 |
| 11 | −0.8 | 0.1998505 | S-NPH3 | 1.4 |
| 12 | 16.42 | 0.396 | | 2 |
| 13 | Infinity | 0.4 | N-ZK7 | 2.8 |
| 14 | Infinity | 0.04 | | 2.8 |
| IMA | Infinity | | | 2.102247 |

TABLE 4

Lens data of Embodiment 4

| Surf | Radius | Thickness | Glass | Clear Diam |
|---|---|---|---|---|
| OBJ | 10 | 8 | | 0 |
| 1 | 4 | 0.59 | N-LASF31A | 5.738571 |
| 2 | 1.55 | 0.705 | | 2.8675 |
| 3 | 4 | 0.1998624 | S-LAH98 | 2.8675 |
| 4 | 0.944 | 0.495 | | 1.74 |
| 5 | 4 | 1.95 | S-LAH79 | 1.74 |
| 6 | −4 | 0.02 | | 1.74 |

TABLE 4-continued

Lens data of Embodiment 4

| Surf | Radius | Thickness | Glass | Clear Diam |
|---|---|---|---|---|
| STO | Infinity | 0.02 | | 0.3347869 |
| 8 | Infinity | 1.065 | N-LAK336 | 1.74 |
| 9 | −1.122 | 0.02 | | 1.74 |
| 10 | 2.925 | 0.745 | S-LAH59 | 1.44 |
| 11 | −0.8 | 0.27 | S-NPH2 | 1.44 |
| 12 | 6.0525 | 0.3938605 | | 1.74 |
| 13 | Infinity | 0.4 | N-ZK7 | 2.8 |
| 14 | Infinity | 0.04 | | 2.8 |
| IMA | Infinity | | | 2.113744 |

TABLE 5

Lens data of Embodiment 5

| Surf | Radius | Thickness | Glass | Clear Diam |
|---|---|---|---|---|
| OBJ | 10 | 8 | | 0 |
| 1 | 4.470595 | 0.64 | N-LASF31A | 6.559377 |
| 2 | 1.75 | 0.8989142 | | 3.295538 |
| 3 | 5.033335 | 0.25 | S-LAH98 | 3.295538 |
| 4 | 1.0292 | 0.7127569 | | 1.908204 |
| 5 | −7.05 | 1.318777 | N-SF5 | 1.904173 |
| 6 | −10.46952 | 0.01993368 | | 1.904173 |
| 7 | 2.44618 | 1.005609 | S-T1H57 | 1.340317 |
| 8 | −5.766399 | 0.2006649 | | 1.340317 |
| STO | Infinity | 0.1880398 | | 0.3875774 |
| 10 | 2.461588 | 0.1998451 | N-5F66 | 1.2 |
| 11 | 0.9250964 | 0.6519993 | S-FPM2 | 1.2 |
| 12 | −1.436212 | 0.01971113 | | 1.2 |
| 13 | 4.717489 | 0.1996736 | SF57HTUL-TRA | 1.7 |
| 14 | 0.9249851 | 0.8086821 | N-LASF41 | 1.7 |
| 15 | 6.792067 | 0.325 | | 1.66361 |
| 16 | Infinity | 0.4 | N-ZK7 | 2.8 |
| 17 | Infinity | 0.04 | | 2.8 |
| IMA | Infinity | | | 2.133736 |

TABLE 6

Lens data of Embodiment 6

| Surf | Radius | Thickness | Glass | Clear Diam |
|---|---|---|---|---|
| OBJ | 10 | 8 | | 0 |
| 1 | 3.457952 | 0.465 | N-LASF31A | 5.267703 |
| 2 | 1.433196 | 0.8250966 | | 2.731529 |
| 3 | 5.172053 | 0.205 | N-LASF31A | 2.731529 |
| 4 | 0.851609 | 0.305 | | 1.575477 |
| 5 | 1.352223 | 0.264521 | L-LAH91 | 1.550358 |
| 6 | 0.7774331 | 0.16 | | 1.220027 |
| 7 | 1.420964 | 0.5499949 | S-LAH93 | 1.220027 |
| 8 | −2.37154 | 0.025 | | 1.220027 |
| 9 | −1.973259 | 0.4522523 | N-LAK7 | 1.220027 |
| 10 | −1.241067 | 0.03150913 | | 1.220027 |
| STO | Infinity | 0.2157904 | | 0.4668453 |
| 12 | −4.307316 | 0.3943424 | S-LAH65V | 1.220027 |
| 13 | −1.300063 | 0.02 | | 1.220027 |
| 14 | 3.031296 | 0.7344458 | N-LAK336 | 1.22755 |
| 15 | 0.7485767 | 0.4092024 | S-NPH3 | 1.303808 |
| 16 | −6.679741 | 0.223 | | 1.684501 |
| 17 | Infinity | 0.4 | N-ZK7 | 2.8 |
| 18 | Infinity | 0.04 | | 2.8 |
| IMA | Infinity | | | 2.133043 |

TABLE 7

Lens data of Embodiment 7

| Surf | Radius | Thickness | Glass | Clear Diam |
|---|---|---|---|---|
| OBJ | 10 | 8 | | 0 |
| 1 | 5.111192 | 1.3 | S-NBH55 | 7.762728 |
| 2 | 1.337 | 0.7524318 | | 2.529821 |
| 3 | 5.351464 | 0.2 | S-NBH55 | 2.529821 |
| 4 | 0.8152746 | 0.3556025 | | 1.466356 |
| 5 | 2.527006 | 1.164849 | N-5F66 | 1.460702 |
| 6 | −4.35126 | 0.06336355 | | 1.460702 |
| STO | Infinity | 0.01969143 | | 0.2854687 |
| 8 | −36.85842 | 0.7725588 | S-LAH97 | 1.460702 |
| 9 | −0.9044592 | 0.01950727 | | 1.460702 |
| 10 | 3.323635 | 0.7508668 | S-LAH64 | 1.205833 |
| 11 | −0.7232511 | 0.2031823 | S-NPH3 | 1.290018 |
| 12 | −9.779682 | 0.324 | | 1.579365 |
| 13 | Infinity | 0.4 | N-ZK7 | 2.8 |
| 14 | Infinity | 0.04 | | 2.8 |
| IMA | Infinity | | | 2.148502 |

TABLE 8

Lens data of Embodiment 8

| Surf | Radius | Thickness | Glass | Clear Diam |
|---|---|---|---|---|
| OBJ | 10 | 8 | | 0 |
| 1 | 6.19235 | 1.182976 | N-BK7 | 8.692166 |
| 2 | 1.337 | 0.633347 | | 2.52571 |
| 3 | 3.182967 | 0.2 | LASF35 | 2.52571 |
| 4 | 0.8152746 | 0.3666209 | | 1.494221 |
| 5 | 2.237081 | 1.224584 | N-5F66 | 1.487515 |
| 6 | −7.384379 | 0.02 | | 1.487515 |
| STO | −7.384379 | 0.03342331 | | 0.2814958 |
| 8 | −8.916423 | 0.6581249 | S-LAH65VS | 1.487515 |
| 9 | −0.9127536 | 0.01998613 | | 1.487515 |
| 10 | 3.656165 | 0.9232674 | N-LASF31A | 1.230488 |
| 11 | −0.7223008 | 0.3520501 | S-NPH3 | 1.358825 |
| 12 | −29.90218 | 0.22 | | 1.724946 |
| 13 | Infinity | 0.4 | N-ZK7 | 2.8 |
| 14 | Infinity | 0.04 | | 2.8 |
| IMA | Infinity | | | 2.179126 |

TABLE 9

Miscellaneous data of Embodiments 1 to 8

Figure 3:
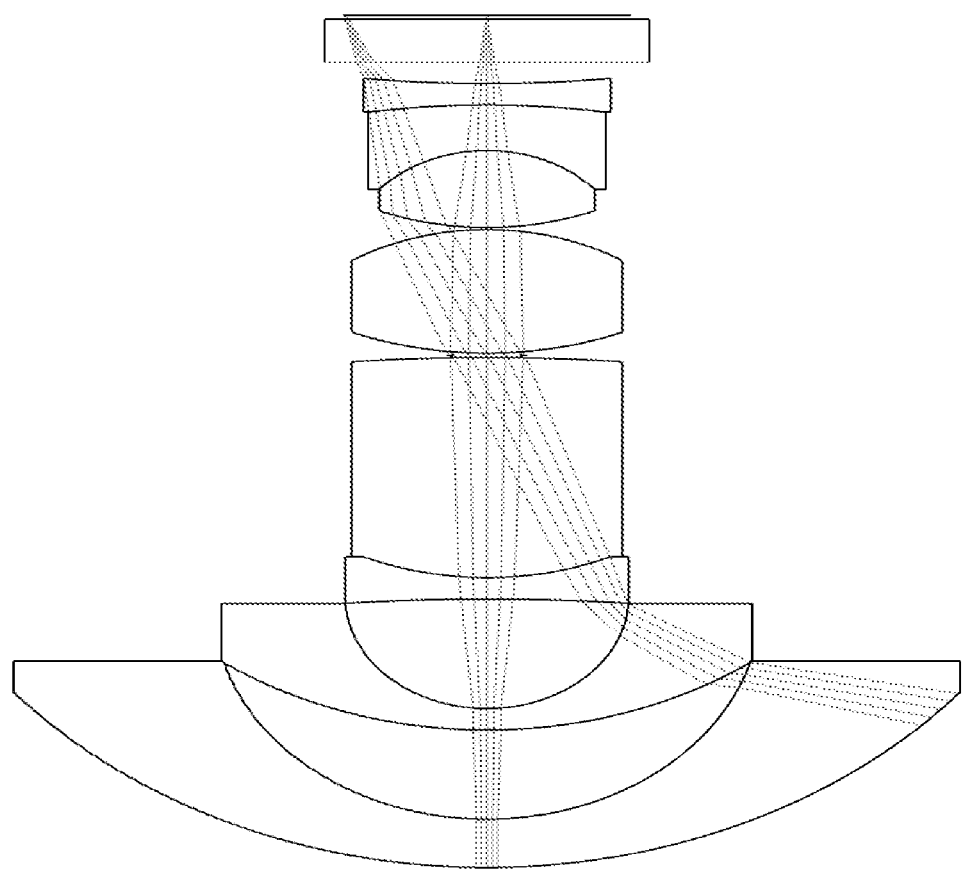
FIG. 3 shows an embodiment 1 of a sensor system according to the invention.
Figure 4:
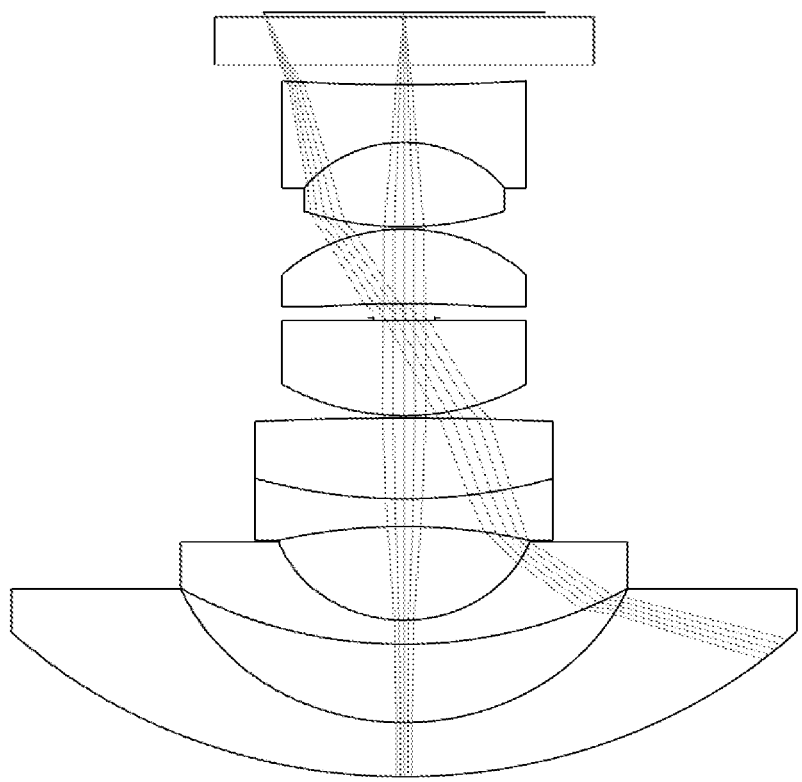
FIG. 4 shows an embodiment 2 of a sensor system according to the invention.
Figure 5:
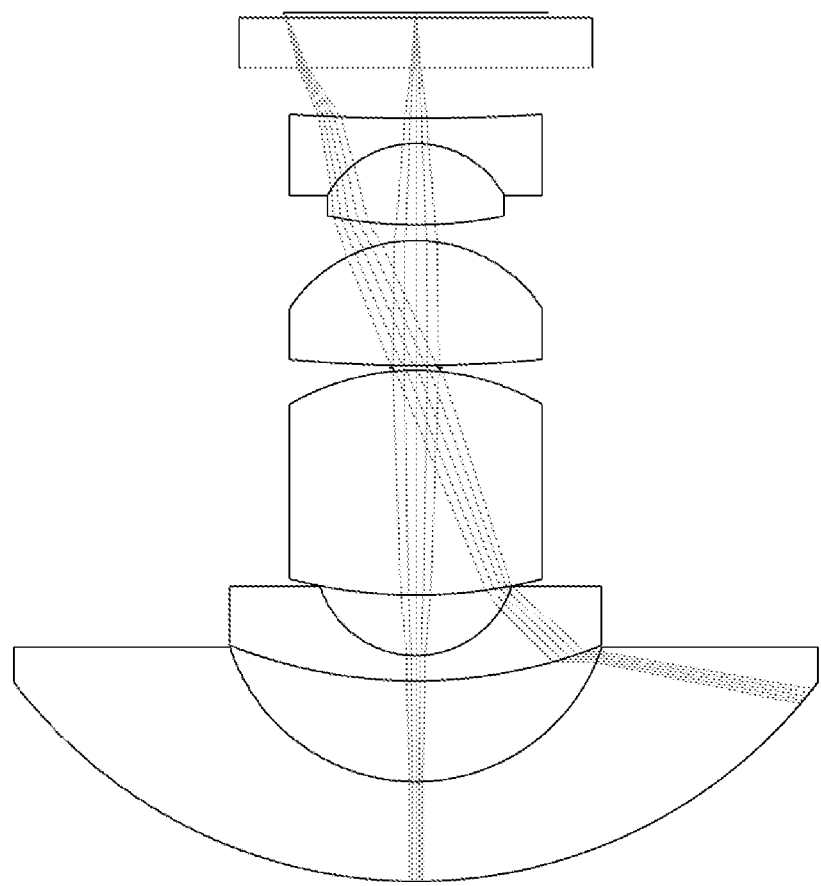
FIG. 5 shows an embodiment 3 of a sensor system according to the invention.
Figure 6:
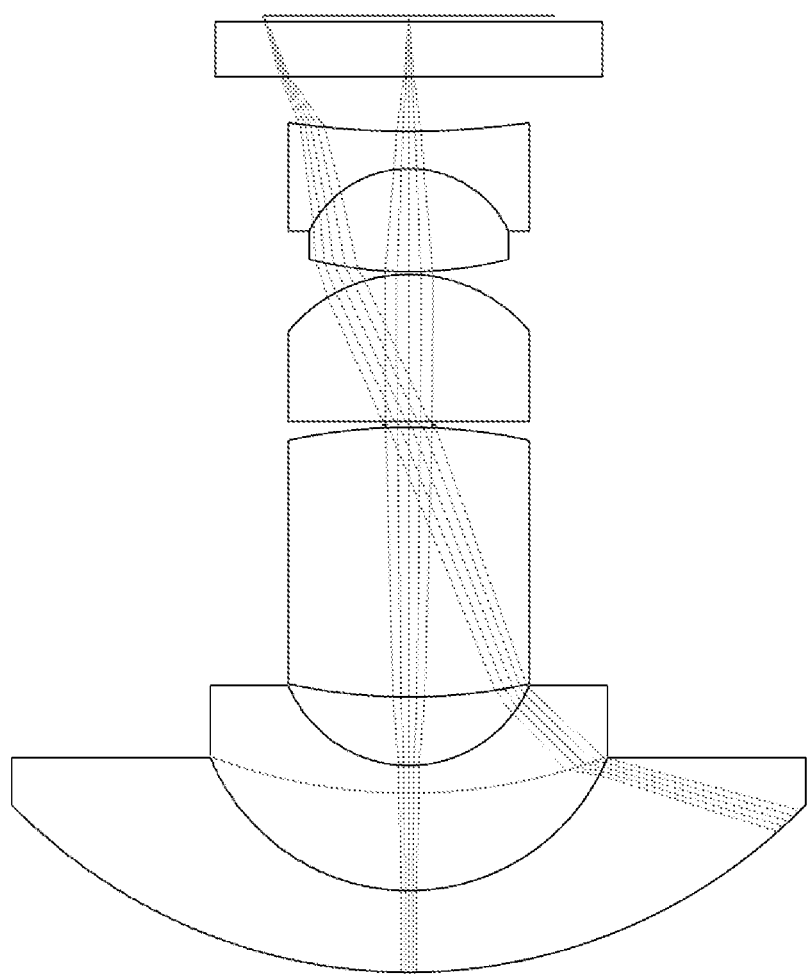
FIG. 6 shows an embodiment 4 of a sensor system according to the invention.
Figure 7:
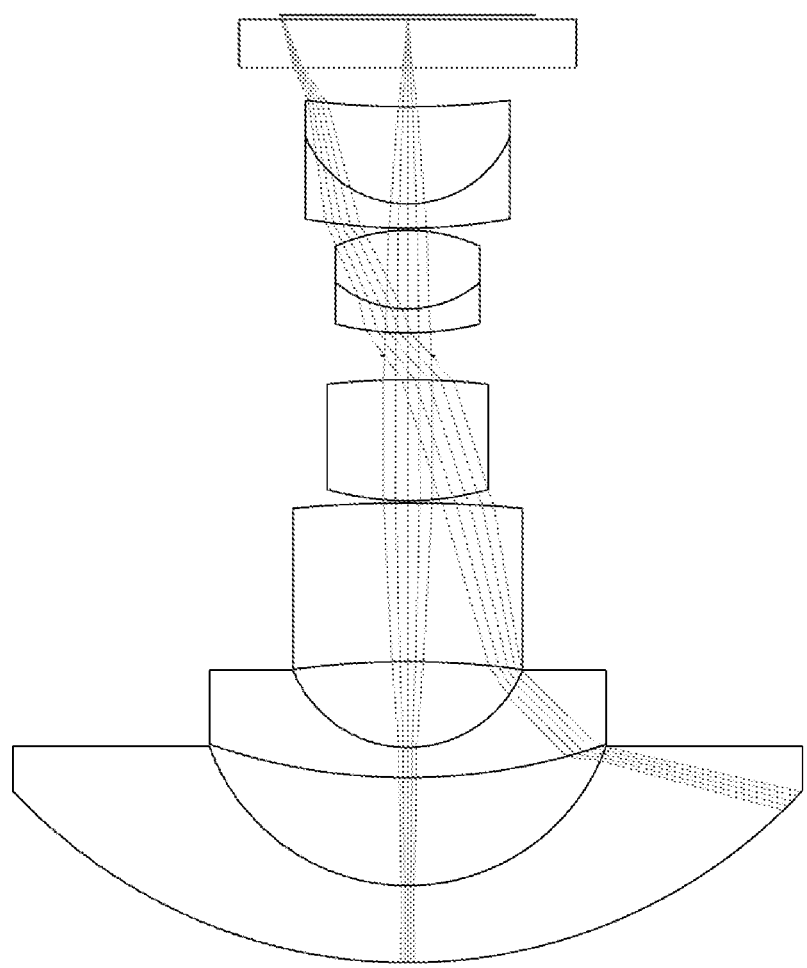
FIG. 7 shows an embodiment 5 of a sensor system according to the invention.
Figure 8:
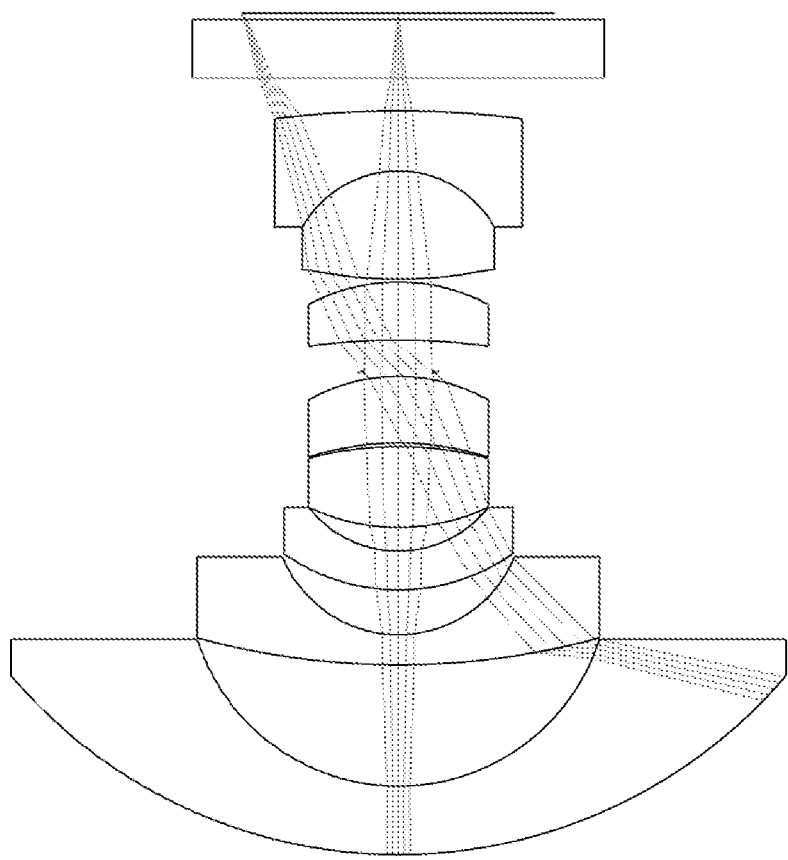
FIG. 8 shows an embodiment 6 of a sensor system according to the invention.
Figure 9:
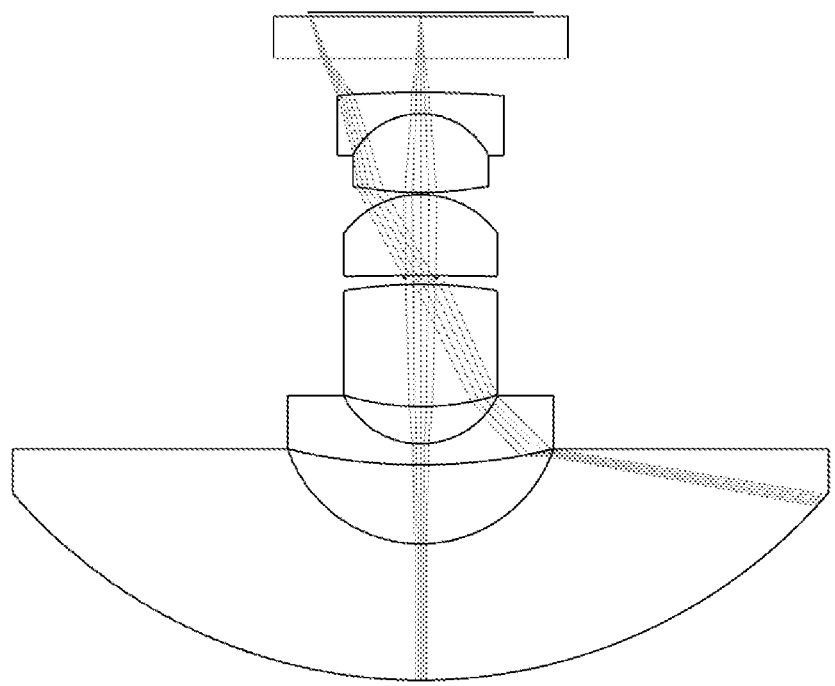
FIG. 9 shows an embodiment 7 of a sensor system according to the invention.
Figure 10:
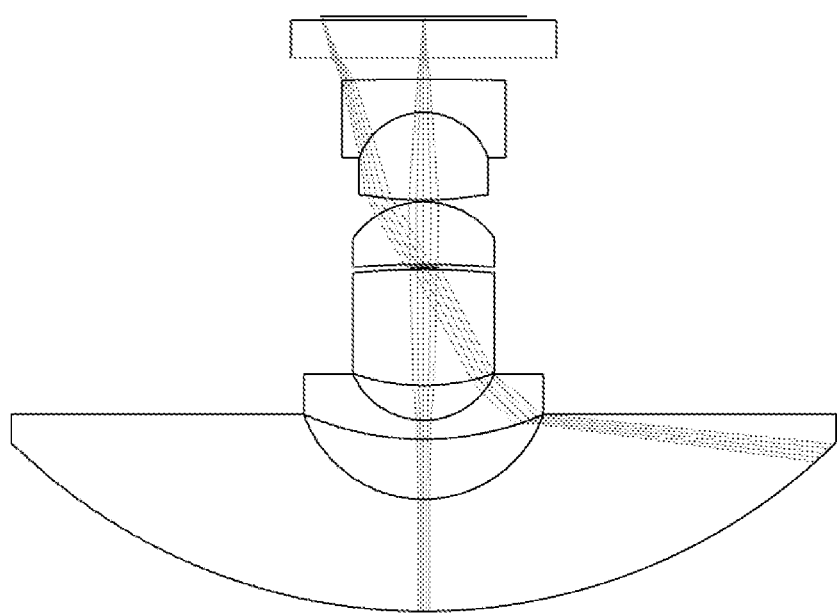
FIG. 10 shows an embodiment 8 of a sensor system according to the invention.
Figure 11:
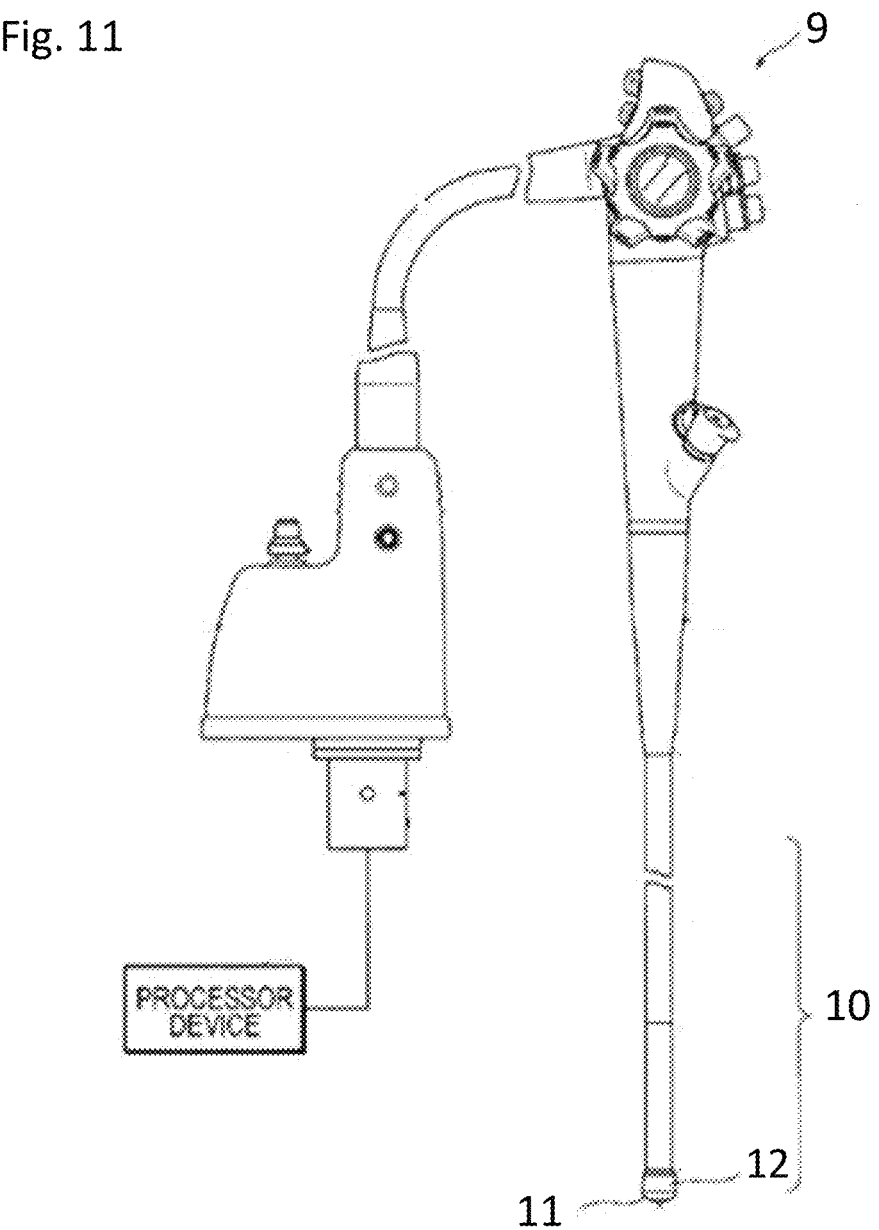
FIG. 11 shows the general set up of the endoscope according to some embodiments of the invention.

| Emb. # | FIG. | F-No. | f [mm] | TTL [mm] | FOV [°] | φ front lens/r4 | r2/r4 | r4/r3 | r2/r3 | r1/r4 |
|---|---|---|---|---|---|---|---|---|---|---|
| 1 | FIG. 3 | 2.8 | 0.54 | 7.937 | 235 | 6.66667 | 1.92952 | 0.31579 | 0.60932 | 4.34190 |
| 2 | FIG. 4 | 4 | 0.535 | 6.354 | 230 | 5.88832 | 1.80711 | 0.31122 | 0.56240 | 4.16244 |
| 3 | FIG. 5 | 4 | 0.526 | 6.886 | 230 | 7.96375 | 1.93750 | 0.20000 | 0.38750 | 5.00000 |
| 4 | FIG. 6 | 4 | 0.528 | 6.914 | 230 | 6.07945 | 1.64195 | 0.23600 | 0.38750 | 4.23729 |
| 5 | FIG. 7 | 4 | 0.517 | 8.228 | 235 | 6.08649 | 1.70068 | 0.20872 | 0.35497 | 4.17881 |
| 6 | FIG. 8 | 2.8 | 0.524 | 5.72 | 235 | 6.19036 | 1.68390 | 0.16454 | 0.27707 | 4.06345 |
| 7 | FIG. 9 | 4 | 0.5225 | 6.366 | 235 | 9.52165 | 1.63989 | 0.15236 | 0.24986 | 6.26886 |
| 8 | FIG. 10 | 4 | 0.5524 | 6.274 | 240 | 10.66111 | 1.63989 | 0.25614 | 0.42004 | 7.59475 |

TABLE 10

| Glass | Refractive index nd | Abbe number vd |
|---|---|---|
| N-LASF31A | 1.883 | 40.76 |
| S-NBH55 | 1.8 | 29.84 |
| N-BK7 | 1.5168 | 64.17 |
| LASF35 | 2.02204 | 29.06 |
| S-LAH98 | 1.95375 | 32.32 |
| S-LAH88 | 1.9165 | 31.6 |
| L-LAH91 | 1.7645 | 49.09 |

TABLE 10-continued

| Glass | Refractive index nd | Abbe number vd |
|---|---|---|
| S-LAH93 | 1.90525 | 35.04 |
| S-LAH55 | 1.83481 | 42.7 |
| N-SF5 | 1.67271 | 32.25 |
| N-LAK7 | 1.6516 | 58.52 |
| N-LAK33B | 1.755 | 52.3 |
| N-LAK34 | 1.72916 | 54.5 |
| N-BAK4 | 1.56883 | 55.98 |
| S-TIH57 | 1.963 | 24.11 |
| N-5F66 | 1.92286 | 20.88 |
| S-FPM2 | 1.59522 | 67.74 |
| S-LAH79 | 2.0033 | 28.3 |
| S-LAH59 | 1.816 | 46.6 |
| S-LAH64 | 1.788 | 47.4 |
| S-LAH65V | 1.804 | 46.6 |
| S-LAH65VS | 1.804 | 46.53 |
| S-LAH97 | 1.755 | 52.32 |
| S-LAL19 | 1.72916 | 54.09 |
| S-LAL7 | 1.6516 | 58.55 |
| N-SF57HULTRA | 1.84666 | 23.78 |
| N-LASF41 | 1.83501 | 43.13 |
| S-NPH3 | 1.95906 | 17.47 |
| S-NPH2 | 1.92286 | 18.9 |
| N-ZK7 | 1.50847 | 61.19 |

The following aspects belong to the original invention:

1. Objective lens, consisting of, in order from an object side to an image side:

a first meniscus lens having a convex side towards the object side;

a second meniscus lens having a convex side towards the object side;

a first condensing unit configured to condense light from the second meniscus lens;

an aperture stop;

a second condensing unit configured to condense light from the aperture stop; wherein an apex of the second meniscus lens is spaced apart from the first meniscus lens;

a total number of lenses in the first and second condensing units is not less than 4 and not more than 6;

if a radius of the first meniscus lens on the image side is denoted r2, a radius of the second meniscus lens on the object side is denoted r3, and a radius of the second meniscus lens on the image side is denoted r4, at least two of the following three conditions are fulfilled:

$r2/r4 \geq 1.40$;

$r4/r3 \geq 0.111$; and $r2/r3 \geq 0.16$.

2. The objective lens according to aspect 1, wherein at least one of the following conditions is fulfilled:

$1.98 \geq r2/r4$;

$0.35 \geq r4/r3$; and $0.65 \geq r2/r3$.

3. The objective lens according to any of aspects 1 and 2, wherein at least one of the following conditions is fulfilled:

$r2/r4 \geq 1.64$;

$r4/r3 \geq 0.19$; and $r2/r3 \geq 0.35$.

4. The objective lens according to any of aspects 1 to 3, wherein at least one of the following conditions is fulfilled:
the first condensing unit consists of one lens or two lenses or three lenses; and
the second condensing unit consists of three lenses or four lenses.

5. The objective lens according to any of aspects 1 to 4, wherein a field of view of the objective lens is not less than 225°.

6. The objective lens according to any of aspects 1 to 5, wherein,
if a radius of the first meniscus lens on the object side is denoted r1, the following condition is fulfilled:

$4.0 \leq r1/r4 \leq 7.6$.

7. The objective lens according to any of aspects 1 to 6, wherein at least one of the following conditions is fulfilled:
a sum of a refractive index of the first meniscus lens and a refractive index of the second meniscus lens is not less than 3.56; and
a sum of an Abbe number of the first meniscus lens and an Abbe number of the second meniscus lens is not less than 58, wherein
the refractive indices are determined at a wavelength of 587.6 nm.

8. The objective lens according to any of aspects 1 to 7, wherein a diameter of the first meniscus lens is not larger than 7 mm.

9. A sensor system comprising
an objective lens according to any of aspects 1 to 8;
a sensor device configured to convert photoelectrically an image formed by the objective lens on a sensor area into an electrical signal; and
a cover glass covering the sensor area, wherein the cover glass is located between the second condensing unit and the sensor area.

10. The sensor system according to aspect 9, wherein an image circle of a sphere located 8 mm in front of an apex of the first meniscus lens on the sensor area is included in the sensor area.

11. The sensor system according to aspect 10, wherein an optical length from an apex of the first meniscus lens to the sensor area is not more than 10 mm.

12. The sensor system according to aspect 11, wherein a chief ray angle at each location of the image circle is not larger than 30°.

13. The sensor system according to any of aspects 11 and 12, wherein, if the diameter of the image circle is denoted di, a field of view of the objective lens is denoted FOV, a diameter of the first meniscus lens is denoted d1, and an f-number of the objective lens is denoted F, the following condition is fulfilled:

$64 \leq (di*FOV)/(d1*F)$.

14. An endoscope comprising a tube and a head at a distal end of the tube, wherein the head comprises a sensor system according to any of aspects 9 to 13.

The invention claimed is:
1. An objective lens, comprising, in order from an object side to an image side:
a first meniscus lens having a convex side towards the object side;
a second meniscus lens having a convex side towards the object side;
a first condenser configured to condense light from the second meniscus lens;
an aperture stop;
a second condenser configured to condense light from the aperture stop; wherein
an apex of the second meniscus lens is spaced apart from the first meniscus lens;
a total number of lenses in the first and second condensers is not less than 4 and not more than 6;
a radius of the first meniscus lens on the object side is denoted r1, a radius of the first meniscus lens on the image side is denoted r2, a radius of the second meniscus lens on the object side is denoted r3, and a radius of the second meniscus lens on the image side is denoted r4, and the following four conditions are fulfilled:

$1.98 \geq r2/r4 \geq 1.40$;

$0.35 \geq r4/r3$;

$0.65 \geq r2/r3 \geq 0.16$; and $4.0 \leq r1/r4 \leq 7.6$, characterized in that the following condition is fulfilled:

$r4/r3 \geq 0.152$.

a field of view (FOV) is 225 degrees or more, and
wherein an F-number (F-No), a focal length (f) and a total lens length (TTL) of the objective lens are selected from a group consisting of: F-No: 2.8, f: 0.54, TTL: 7.937; F-No: 4, f: 535, TTL: 6.354; F-No: 4, f: 0.526, TTL: 6.886; F-No: 4, f: 0.528, TTL: 6.914; F-No: 4, f: 0.517, TTL: 8.228; F-No: 2.8, f: 0.524, TTL: 5.72; F-No: 4, f: 0.5225, TTL: 6.366; F-No: 4, f: 0.5524, TTL: 6.274.

2. An objective lens, comprising, in order from an object side to an image side:
a first meniscus lens having a convex side towards the object side;
a second meniscus lens having a convex side towards the object side;
a first condenser configured to condense light from the second meniscus lens;
an aperture stop;
a second condenser configured to condense light from the aperture stop; wherein
an apex of the second meniscus lens is spaced apart from the first meniscus lens;
a total number of lenses in the first and second condensers is not less than 4 and not more than 6;
a radius of the first meniscus lens on the object side is denoted r1, a radius of the first meniscus lens on the image side is denoted r2, a radius of the second meniscus lens on the object side is denoted r3, and a radius of the second meniscus lens on the image side is denoted r4, and the following four conditions are fulfilled:

$1.98 \geq r2/r4 \geq 1.40$;

$0.35 \geq r4/r3$;

$0.65 \geq r2/r3 \geq 0.16$; and $4.0 \leq r1/r4 \leq 7.6$, characterized in that the following condition is fulfilled:

$r4/r3 \geq 0.152$.

a field of view (FOV) is 225 degrees or more, and wherein an F-number (F-No) of the objective lens, and a focal length (f) of the objective lens are selected from a group consisting of F-No: 2.8, f: 0.54; F-No: 4, f: 0.535; F-No: 4, f: 0.526; F-No: 4, f: 0.528; F-No: 4, f: 0.517; F-No: 2.8, f: 0.524; F-No: 4, f: 0.5225; F-No: 4, f: 0.5524.

* * * * *